United States Patent
Wakabayashi et al.

(10) Patent No.: US 11,547,278 B2
(45) Date of Patent: Jan. 10, 2023

(54) ENDOSCOPE FRONT-END STRUCTURE AND ENDOSCOPE

(71) Applicant: OLYMPUS CORPORATION, Tokyo (JP)

(72) Inventors: Toru Wakabayashi, Tokyo (JP); Nau Satake, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 11 days.

(21) Appl. No.: 17/145,477

(22) Filed: Jan. 11, 2021

(65) Prior Publication Data
US 2021/0127958 A1 May 6, 2021

Related U.S. Application Data

(63) Continuation of application No. PCT/JP2018/027724, filed on Jul. 24, 2018.

(51) Int. Cl.
*A61B 1/00* (2006.01)
*A61B 1/05* (2006.01)
(Continued)

(52) U.S. Cl.
CPC ........ *A61B 1/0011* (2013.01); *A61B 1/00009* (2013.01); *A61B 1/051* (2013.01);
(Continued)

(58) Field of Classification Search
CPC ... A61B 1/051; A61B 1/00009; A61B 1/0011; A61B 1/00114; A61B 1/07; A61B 1/00128; H04N 7/183
See application file for complete search history.

(56) References Cited

U.S. PATENT DOCUMENTS

2012/0197081 A1\* 8/2012 Kimura ............. A61B 1/00124
600/110
2014/0093209 A1\* 4/2014 Jono .................... G02B 6/4234
385/115
(Continued)

FOREIGN PATENT DOCUMENTS

JP S59-124313 A 7/1984
JP H09-098944 A 4/1997
(Continued)

OTHER PUBLICATIONS

International Search Report dated Sep. 11, 2018 issued in PCT/EP2018/027724.

*Primary Examiner* — Nasim N Nirjhar
(74) *Attorney, Agent, or Firm* — Scully, Scott, Murphy & Presser, P.C.

(57) ABSTRACT

An endoscope front-end structure includes: an imaging module; a frame body that has a through hole and a salient portion, the frame body being configured to hold the imaging module when the imaging module is inserted in the through hole from an insertion opening formed at a proximal end of the frame body; a first adhesive agent that is filled and hardened between a part of outer periphery of a resin seal and a surface of the salient portion; and a second adhesive agent that is filled and hardened in a gap formed between the through hole of the frame body and the imaging module inserted in the through hole.

8 Claims, 7 Drawing Sheets

(51) Int. Cl.
*H04N 7/18* (2006.01)
*A61B 1/07* (2006.01)
(52) U.S. Cl.
CPC .......... *H04N 7/183* (2013.01); *A61B 1/00114* (2013.01); *A61B 1/07* (2013.01)

(56) References Cited

U.S. PATENT DOCUMENTS

| | | | | |
|---|---|---|---|---|
| 2016/0157705 | A1* | 6/2016 | Wataya | A61B 1/051 600/104 |
| 2017/0059848 | A1* | 3/2017 | Haraguchi | G02B 23/2469 |
| 2017/0255001 | A1* | 9/2017 | Yamashita | H04N 5/2253 |
| 2018/0081143 | A1 | 3/2018 | Shimono et al. | |

FOREIGN PATENT DOCUMENTS

| | | | |
|---|---|---|---|
| JP | 2001-128930 A | 5/2001 | |
| JP | 2004-8638 A | 1/2004 | |
| JP | 2015-058118 A | 3/2015 | |
| JP | 2017-086550 A | 5/2017 | |
| JP | 2018-042935 A | 3/2018 | |
| WO | WO 2014/034839 A1 | 3/2014 | |

\* cited by examiner

ENDOSCOPE FRONT-END STRUCTURE AND ENDOSCOPE

CROSS-REFERENCE TO RELATED APPLICATION

This application is a continuation of International Application No. PCT/JP2018/027724, filed on Jul. 24, 2018, the entire contents of which are incorporated herein by reference.

BACKGROUND

1. Technical Field

The present disclosure is related to an endoscope front-end structure and an endoscope.

2. Related Art

In the related art, an endoscope includes an elongated and flexible insertion portion including an imaging module that is installed at an front end of the insertion portion; and the insertion portion is inserted inside the body of a subject such as a patient. Hence, image data of the inside of the body of the subject is obtained using the imaging module and is sent to an external information processing device. From the perspective of protecting the imager present therein, the imaging module is placed into a metallic frame body in which an adhesive agent made of a thermoset resin is filled with the aim of reducing the stress acting on the imager, alleviating the effect of moisture, and fixing the position of the imager (for example, refer to Japanese Laid-open Patent Publication No. 2001-128930).

SUMMARY

In some embodiments, an endoscope front-end structure includes: an imaging module configured to form an image of a photographic subject using an optical unit, generate an image signal by performing photoelectric conversion of photographic subject image, which is formed by the optical unit, using an imager, and transmit the image signal using a cable; a frame body that has a through hole passing through the frame body in an optical axis direction of the optical unit, an inner surface of the through hole being partially open, and has a salient portion protruding from the inner surface of the through hole, the frame body being configured to hold the imaging module when the imaging module is inserted in the through hole from an insertion opening formed at a proximal end of the frame body; a first adhesive agent that is filled and hardened between a part of outer periphery of a resin seal and a surface of the salient portion, the resin seal being configured to seal a portion spanning from a proximal end of a lateral face of the optical unit to a junction of the cable, the part of outer periphery of the resin seal and the surface of the salient portion being bonded with each other via the first adhesive agent; and a second adhesive agent that is filled and hardened in a gap formed between the through hole of the frame body and the imaging module inserted in the through hole, the frame body and the imaging module being bonded with each other via the second adhesive agent.

In some embodiments, an endoscope includes the endoscope front-end structure above.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
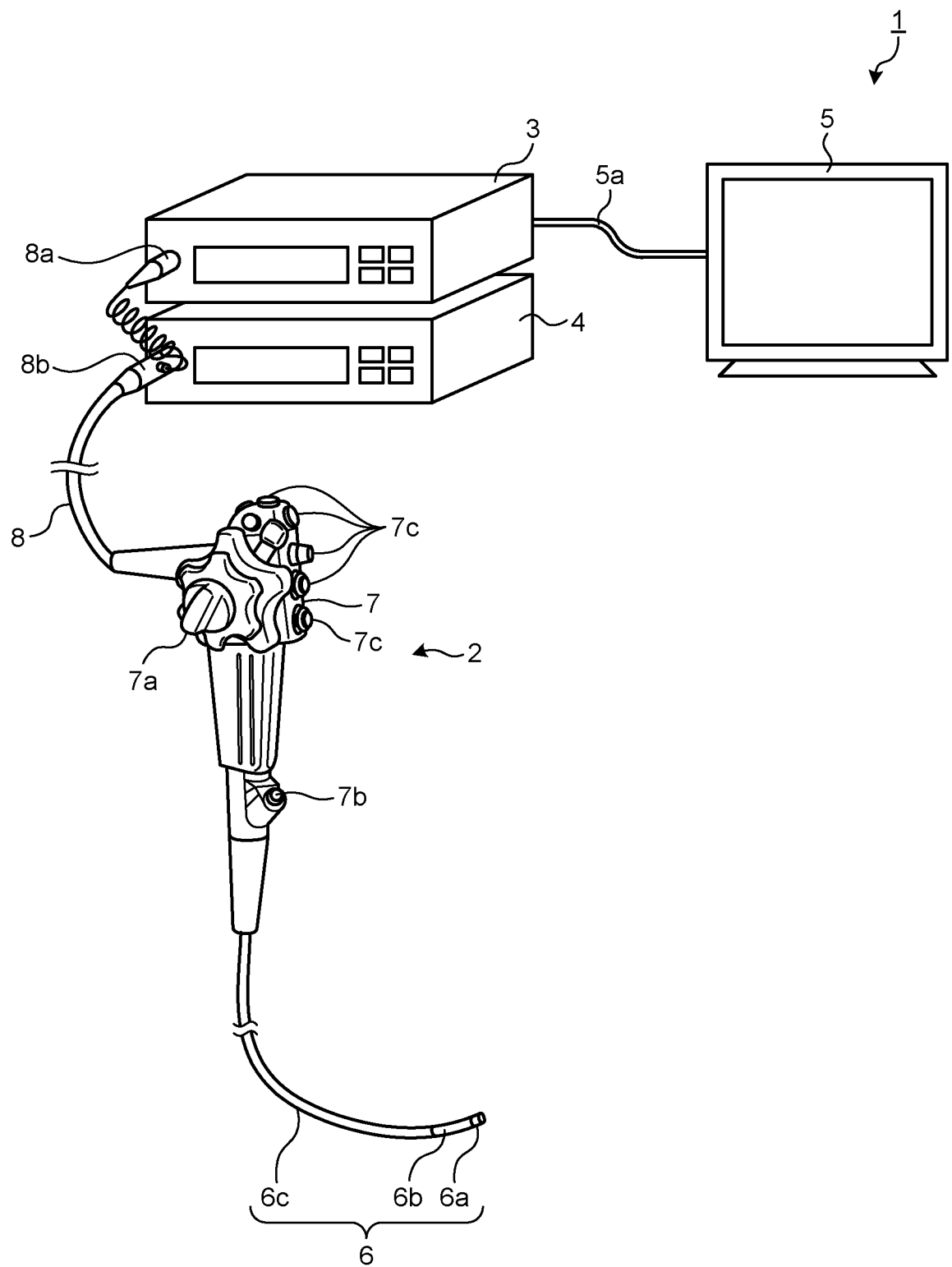
FIG. 1 is a diagram that schematically illustrates an overall configuration of an endoscope system according to an embodiment of the disclosure.

As an exemplary embodiment of the disclosure, the following explanation is given about an endoscope system including an endoscope front-end structure. However, the disclosure is not limited by the embodiment described below. Moreover, the diagrams referred to in the following explanation illustrate the shapes, the sizes, and the positional relationships only in a schematic manner in order to enable understanding of the details of the disclosure. That is, the disclosure is not limited by the shapes, the sizes, and the positional relationships illustrated in the drawings. Furthermore, among the drawings, there are portions having different dimensions and proportions.

Embodiment

FIG. 1 is a diagram that schematically illustrates an overall configuration of an endoscope system 1 according to an embodiment of the disclosure. As illustrated in FIG. 1, the endoscope system 1 according to the embodiment includes an endoscope 2 that is inserted inside the body of a subject, takes images of the inside of the body of the subject, and generates image signals of the inside of the body of the subject; an information processing device 3 that performs predetermined image processing with respect to the image signals obtained by imaging by the endoscope 2 and that controls the constituent elements of the endoscope system 1; a light source device 4 that generates an illumination light to be used by the endoscope 2; and a display device 5 that displays images corresponding to the image signals on which the information processing device 3 has performed image processing.

The endoscope 2 includes an insertion portion 6 to be inserted inside the body of a subject; an operating unit 7 that is present at the proximal end of the insertion portion 6 and that is hand-held by the operator; and a flexible universal code 8 that extends from the operating unit 7.

The insertion portion 6 is implemented using a light guide made of an illumination fiber, and using an electric cable or an optical fiber. The insertion portion 6 includes the following: a front end portion 6a that has an imager (described later) built-in; a freely-bendable curved portion 6b that is made of a plurality of bent pieces; and a flexible tube 6c that is a flexible tube connected to the proximal end of the curved portion 6b. The front end portion 6a has the following components (not illustrated) disposed therein: an illumination unit that illuminates the inside of the subject via an illumination lens; an observation unit that takes images of the inside of the subject; an opening that is communicated with a treatment tool channel; and an insufflation/water supply nozzle.

The operating unit 7 includes the following: a curved knob 7a that is meant for bending the curved portion 6b in the vertical direction and the horizontal direction; a treatment tool insertion portion 7b from which a treatment tool such as a biopsy forceps or a laser knife is insertable inside the body cavity of the subject; and a plurality of switches 7c that enable operations of the peripheral devices such as the information processing device 3, the light source device 4, an insufflation device, a water supply device, and a gas transportation device. The treatment tool that is inserted from the treatment tool insertion portion 7b passes through an internal treatment tool channel and appears from an opening formed at the front end of the insertion portion 6.

The universal cord 8 is configured using a light guide made of an illumination fiber, and using a cable. The universal cord 8 is branched at the proximal end thereof, with one of the branched ends representing a connector 8a and the other branched end representing a connector 8b. The connector 8a is detachably attachable to the connector of the information processing device 3. The connector 8b is detachably attachable to the light source device 4. The universal cord 8 passes on the illumination light, which is supplied from the light source device 4, to the front end portion 6a via the connector 8b and via the light guide made of an illumination fiber. Moreover, the universal cord 8 transmits the image signals, which are obtained as a result of imaging by the imager (described later), to the information processing device 3 via the cable and the connector 8a.

The information processing device 3 performs predetermined image processing on the image signals output from the connector 8a, as well as controls the endoscope system 1 in entirety.

The light source device 4 is configured using a light source that emits light, and using a collecting lens. The light source device 4 emits light from the light source under the control of the information processing device 3; and supplies illumination light, which is to be used for illuminating the inside of the body of the subject representing the photographic subject, to the endoscope 2 that is connected via the connector 8b and via the light guide made of an illumination fiber of the universal cord 8.

The display device 5 is configured using a liquid crystal display or an organic electro Luminescence (EL) display. The display device 5 displays, via a video cable 5a, a variety of information containing images corresponding to the image signals that have been subjected to predetermined image processing by the information processing device 3. Hence, the operator can operate the endoscope 2 while looking at the images (in-vivo images) displayed in the display device 5, and can observe the desired locations inside the subject and can assess the symptoms.

Figure 2:
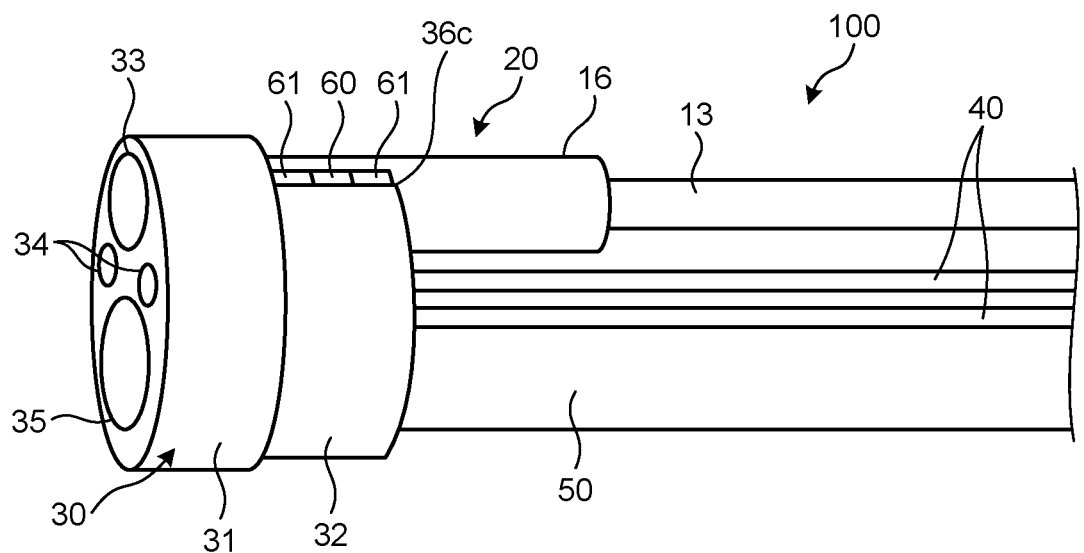
FIG. 2 is a perspective view of an endoscope front-end structure used in the endoscope system illustrated in FIG. 1.
Figure 3:
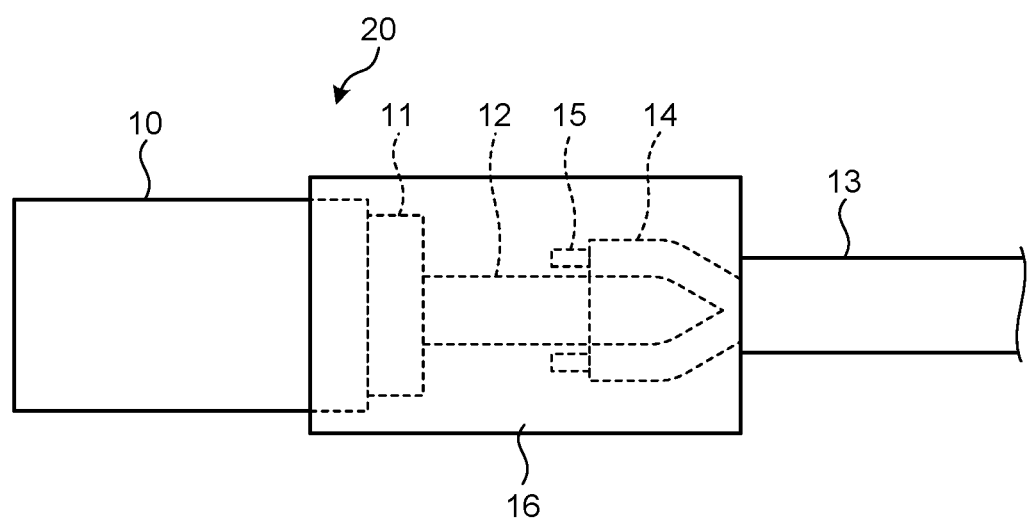
FIG. 3 is a lateral view of an imaging module used in the endoscope front-end structure illustrated in FIG. 2.
Figure 4A:
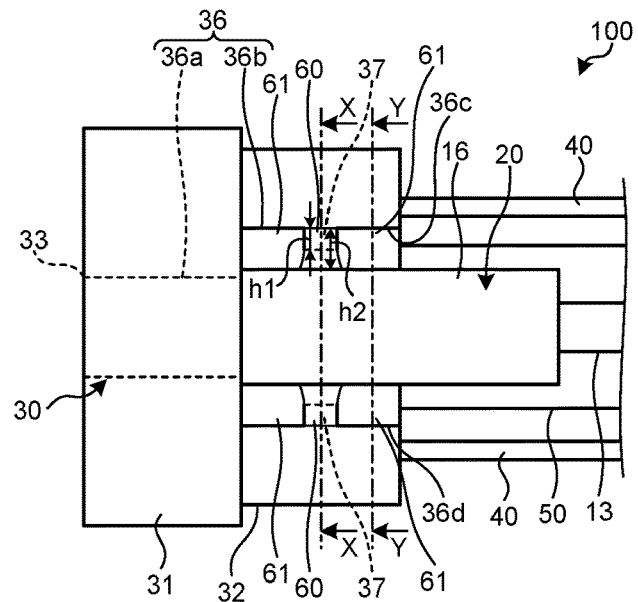
FIG. 4A is a top view of the endoscope front-end structure illustrated in FIG. 2.
Figure 4B:
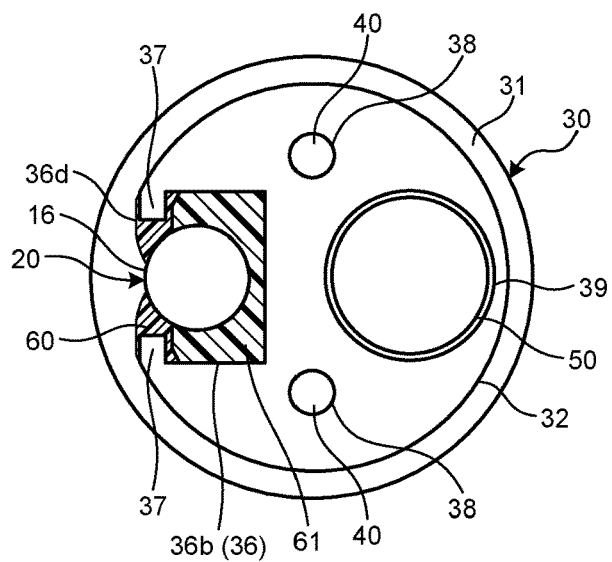
FIG. 4B is an X-X cross sectional view of the endoscope front-end structure illustrated in FIG. 2.
Figure 4C:
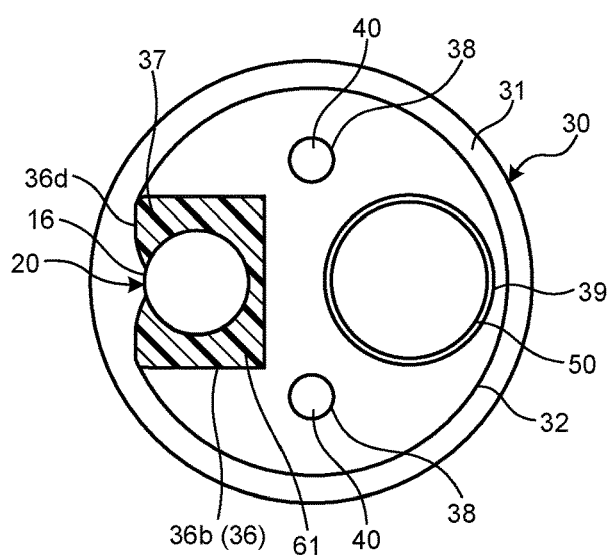
FIG. 4C is a Y-Y cross sectional view of the endoscope front-end structure illustrated in FIG. 2.

Given below is the detailed explanation about the endoscope front-end structure disposed at the front end portion 6a of the endoscope 2. FIG. 2 is a perspective view of an endoscope front-end structure 100 used in the endoscope system 1 illustrated in FIG. 1. FIG. 3 is a lateral view of an imaging module 20 used in the endoscope front-end structure 100 illustrated in FIG. 2. FIG. 4A is a top view of the endoscope front-end structure 100 according to the embodiment of the disclosure; FIG. 4B is a cross sectional view taken along X-X line illustrated in FIG. 4A; and FIG. 4C is a cross sectional view taken along Y-Y line illustrated in FIG. 4A.

The endoscope front-end structure 100 includes the following: the imaging module 20 that forms an image of the photographic subject using an optical unit 10, generates an image signal by performing photoelectric conversion of the photographic subject image, which is formed by the optical unit 10, using an imager 11, and transmits an image signal using signal cables 14; a frame body 30 that has a through hole 36 passing through the frame body 30 in an optical axis direction of the optical unit 10, an inner surface of the through hole being partially open, and that includes salient portions 37 protruding from the inner surface of the through hole 36, the frame body 30 being configured to hold the imaging module 20 when the imaging module 20 is inserted into the through hole 36 from an insertion opening 36c (not illustrated in FIG. 2, illustrated in FIG. 6A) formed at a proximal end of the frame body 30; a first adhesive agent 60 that is filled and hardened between a part of the outer periphery of a resin seal 16 and a surface of the salient portion, the resin seal 16 being configured to seal a portion spanning from a proximal end of a lateral face of the optical unit 10 to a junction of the signal cables 14, the part of outer periphery of the resin seal 16 and the surface of the salient portions 37 being bonded with each other via the first adhesive agent 60; and a second adhesive agent 61 that is filled and hardened in a gap formed between the through hole 36 of the frame body 30 and the imaging module 20 inserted in the through hole 36, the frame body 30 and the imaging module 20 being bonded with each other via the second adhesive agent 61.

Thus, the imaging module 20 includes the optical unit 10 that forms an image of the photographic subject; the imager 11 that generates an image signal by performing photoelectric conversion of the photographic subject image formed by the optical unit 10; a substrate 12 that is connected to the underside of the imager 11; a combined cable 13 formed by bundling a plurality of signal cables 14 connected to the substrate 12; and the resin seal 16.

The optical unit 10 includes a plurality of field lenses (not illustrated) and a lens holder that holds a cover glass.

The imager 11 is configured using a charge-coupled device (CCD) or a complementary metal-oxide semiconductor (CMOS); and the light receiving unit of the imager 11 is covered by and bonded to the cover glass. The imager 11 is held in the lens holder of the optical unit 10 on the other side of the cover glass, which is bonded to the imager 11.

The substrate 12 is electrically and mechanically connected to a connection terminal (not illustrated) formed on the underside of the imager 11. On the substrate 12, cable cores 15 of a plurality of signal cables 14 are connected for the purpose of supplying power to the imager 11 or inputting signals to and outputting signals from the imager 11.

The resin seal 16 is used to seal a portion from a proximal end side of a lateral face of the optical unit 10 to an end portion of the combined cable 13 from which the signal cables 14 are drawn. Thus, the resin seal 16 protects the imager 11, protects a junction between the imager 11 and the cover glass, protects a junction between the imager 11 and the substrate 12, and protects junctions between the substrate 12 and the signal cables 14.

The frame body 30 includes a front-end frame portion 31 and a proximal-end frame portion 32. The proximal-end frame portion 32 is covered by a cladding tube and is formed to have a smaller diameter than the diameter of the front-end frame portion 31. The frame body 30 includes through holes 36, 38, and 39 in which the imaging module 20, a light guide 40, and a channel tube 50 of treatment tools are respectively inserted. As a result, the imaging module 20, the channel tube 50 of treatment tools, and the light guide 40 are held and fixed on the frame body 30. On the front-end face of the frame body 30, an observation window 33, illumination windows 34, and a treatment tool opening 35 are formed.

The through hole 36 is formed to pass through the frame body 30 in the optical axis direction from the front-end frame portion 31 to the proximal-end frame portion 32. The through hole 36 includes a through hole 36a inside the front-end frame portion 31 and a through hole 36b inside the proximal-end frame portion 32. The through hole 36a is formed in a cylindrical shape with the substantially same outer diameter as the outer diameter of the optical unit 10; and The through hole 36b has a rectangular shape that is larger than the shape of the resin seal 16. In the proximal-end frame portion 32, an opening 36d is formed by removing a part of the inner surface of the through hole 36b close to an outer periphery of the proximal-end frame portion 32. The opening 36 in the proximal-end frame portion 32 enables filling of the second adhesive agent 61 in the through hole 36 with ease.

In the through hole 36b, the salient portions 37 are formed to protrude from the inner surface of the through hole 36b. Herein, the salient portions 37 is two and are formed to be faced one another. Each salient portion 37 is formed at the central part of a side of the opening 36d, the side being parallel to the optical axis direction. In the embodiment, although the salient portions 37 are formed in a rectangular shape, it is alternatively possible to form the salient portions 37 in a columnar shape, a semispherical shape, a conical shape, or a square pyramid shape. Regarding a height h1 of the salient portions 37, from the perspective of enabling easy insertion of the imaging module 20 in the through hole 36 and from the perspective of reducing the amount of usage of the first adhesive agent 60, it is desirable that the height h1 is 50% to 70% of a distance h2 of a gap between the inner surface of the through hole 36b and an outer surface of the resin seal 16.

The first adhesive agent 60 bonds the outer periphery on a side of the opening 36d of the resin seal 16 and a surface of the salient portions 37. As illustrated in FIG. 4B, the first adhesive agent 60 bonds and fixes the imaging module 20 to the frame body 30, while covering the surface of the salient portions 37. The first adhesive agent 60 hardens instantaneously and, from the perspective of temporary fixing of the salient portions 37 to the resin seal 16, it is desirable to use an ultraviolet cure adhesive.

In order to bond the salient portions 37 and the resin seal 16, the first adhesive agent 60 is supplied in gaps between the resin seal 16 and the salient portions 37. In that case, from the perspective of preventing dripping of the first adhesive agent 60, it is desirable to use an adhesive with a high degree of pre-hardening viscosity. Moreover, from the perspective of strength and positional accuracy of the temporary bonding of the resin seal 16 and the salient portions 37, it is desirable that the first adhesive agent 60 has a high degree of post-hardening hardness.

After a relative position between the imaging module 20 and the light guide 40 is fixed, the second adhesive agent 61 is filled inside the through hole 36 so as to fix the positions the imaging module 20 and the light guide 40. However, when the second adhesive agent 61 hardens, thermal expansion or thermal contraction thereof occurs and it may result in a position misalignment of the imaging module 20 inside the through hole 36. In order to prevent a position misalignment of the imaging module 20, it is possible to think of using the first adhesive agent 60, which hardens instantaneously, to temporarily fix the imaging module 20, and then using the second adhesive agent 61 to bond and fix the imaging module 20. However, if the first adhesive agent 60 is supplied from the opening 36d in the absence of the salient portions 37, it leads to an increase in the amount of usage of the first adhesive agent 60. As a result, the first adhesive agent 60 spreads inside the through hole 36 and leaches into an area meant for filling the second adhesive agent 61 that is to be used in the permanent fixing. The second adhesive agent 61 not only has the function of fixing the position of the imaging module 20, but also enables achieving reduction in the stress acting on the imaging module 20. Hence, it is not desirable that the area meant for filling the second adhesive agent 61 becomes narrow.

In the embodiment of the disclosure, because of the salient portions 37 formed inside the through hole 36, the clearance between the imaging module 20 and the surface of the through hole 36 is narrowed. That enables achieving reduction in the amount of usage of the first adhesive agent 60, and thus the first adhesive agent 60 can be prevented from leaching out into the area meant for filling the second adhesive agent 61. Moreover, the first adhesive agent 60 bonds and fixes the imaging module 20 to the frame body 30 while covering the surface of the salient portions 37. That enables achieving reduction in the amount of usage of the first adhesive agent 60, and at the same time enables achieving enhancement in the connection strength accompanying an increase in the connection area.

The second adhesive agent 61 is filled in the gap between the through hole 36 and the imaging module 20, and bonds the frame body 30 and the imaging module 20. After the salient portions 37 are bonded and fixed to the resin seal 16 using the first adhesive agent 60, the second adhesive agent 61 is supplied in the gap between the through hole 36 and the resin seal 16 from the opening 36d present on the left and right sides of the first adhesive agent 60 that has hardened. As far as the second adhesive agent 61 is concerned, it is desirable to use a thermoset adhesive.

From the perspective of enabling easy filling of the second adhesive agent 61 in the opening 36d, it is desirable that the second adhesive agent 61 has a low degree of pre-hardening viscosity. Herein, it is desirable that the second adhesive agent 61 has a lower degree of pre-hardening viscosity than the degree of pre-hardening viscosity of the first adhesive agent 60.

When some stress is acting on the endoscope front-end structure 100, from the perspective of preventing breakage of the imager 11, it is desirable that the second adhesive agent 61 has a low degree of post-hardening hardness. Herein, it is desirable that the second adhesive agent 61 has a low degree of post-hardening hardness than the degree of post-hardening hardness of the first adhesive agent 60.

In the embodiment of the disclosure, since the salient portions 37 and the resin seal 16 are bonded and fixed using the first adhesive agent 60, the position misalignment of the imaging module 20 can be prevented from occurring even at the time of thermal expansion and thermal contraction accompanying the hardening of the second adhesive agent 61. Moreover, as a result of forming the salient portions 37, the amount of usage of the first adhesive agent 60 can be reduced; the first adhesive agent 60 can be prevented from leaching out in the area meant for filling the second adhesive agent 61; and the risk of breakage of the imager 11 can be reduced when there is stress acting on the endoscope front-end structure 100.

Figure 5A:
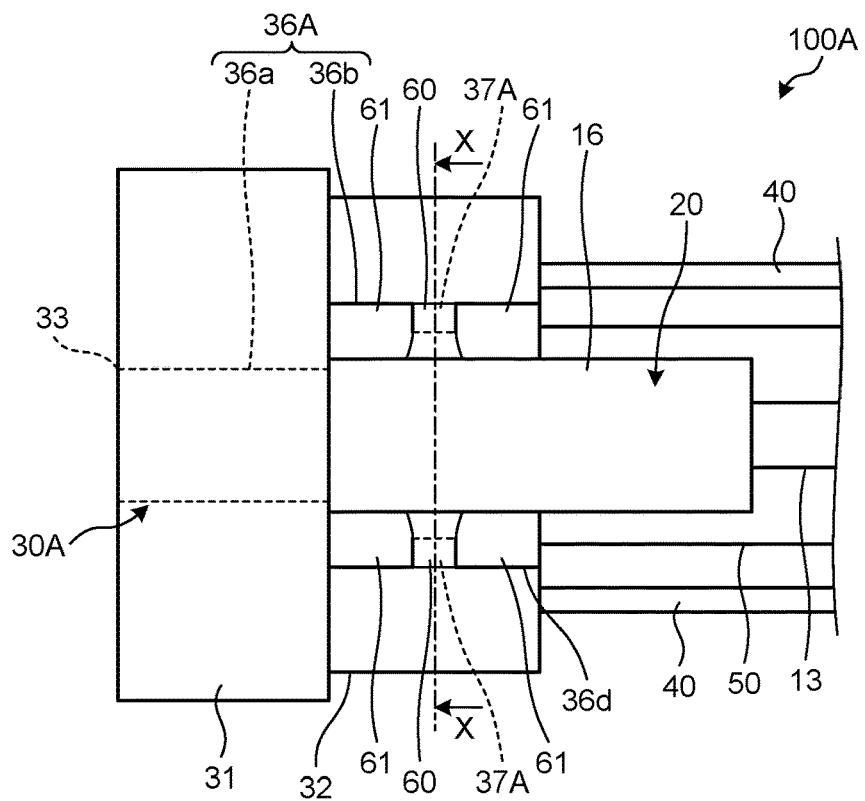
FIG. 5A is a top view of an endoscope front-end structure according to a first modification example of the embodiment of the disclosure.
Figure 5B:
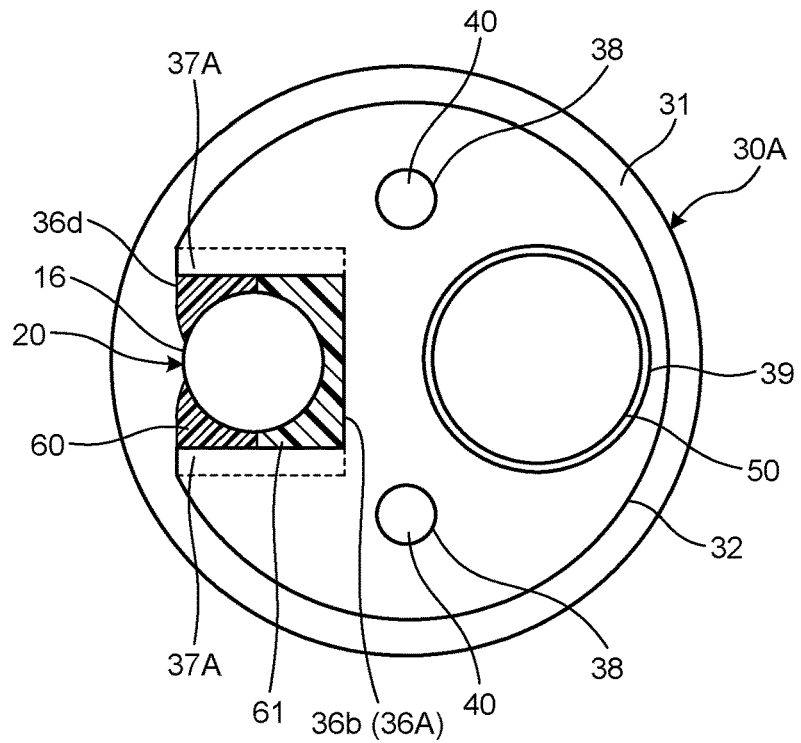
FIG. 5B is an X-X cross sectional view.

In the embodiment described above, although the salient portions 37 are formed to protrude in the opening 36d, they can alternatively be formed in a track-like manner spanning from the opening 36d up to a bottom of the through hole 36b. The bottom of the through hole 36b is an inner surface of the through hole 36b and faces the opening 36d. FIG. 5A is a top view of an endoscope front-end structure 100A according to a first modification example of the embodiment of the disclosure; and FIG. 5B is a cross sectional view taken along X-X line illustrated in FIG. 5A.

In the endoscope front-end structure 100A according to the first modification example, in the through hole 36b of a frame body 30A, salient portions 37A are formed that protrude in a track-like manner spanning from the opening 36d of the through hole 36b up to the bottom of the through hole 36b. As a result of forming the salient portions 37A, the clearance between a through hole 36A and the imaging module 20 is narrowed, so that the salient portions 37A and the resin seal 16 can be bonded and fixed using the first adhesive agent 60 as illustrated in FIG. 5A; the amount of usage of the first adhesive agent 60 can be reduced; and the first adhesive agent 60 can be prevented from leaching out into the area meant for filling the second adhesive agent 61. In the first modification example, the salient portions 37A are formed spanning from the opening 36d up to the bottom of the through hole 36b. Hence, although the salient portions 37A are inferior to the salient portions 37 from the perspective of bonding strength and amount of usage, the salient portions 37A can be manufactured with more ease. Meanwhile, in the endoscope front-end structure 100A too, the cross sectional view perpendicular to the optical axis direction of the proximal-end frame portion 32, in which the salient portions 37A are not formed, has an identical structure to the structure illustrated in FIG. 4C.

Figure 6A:
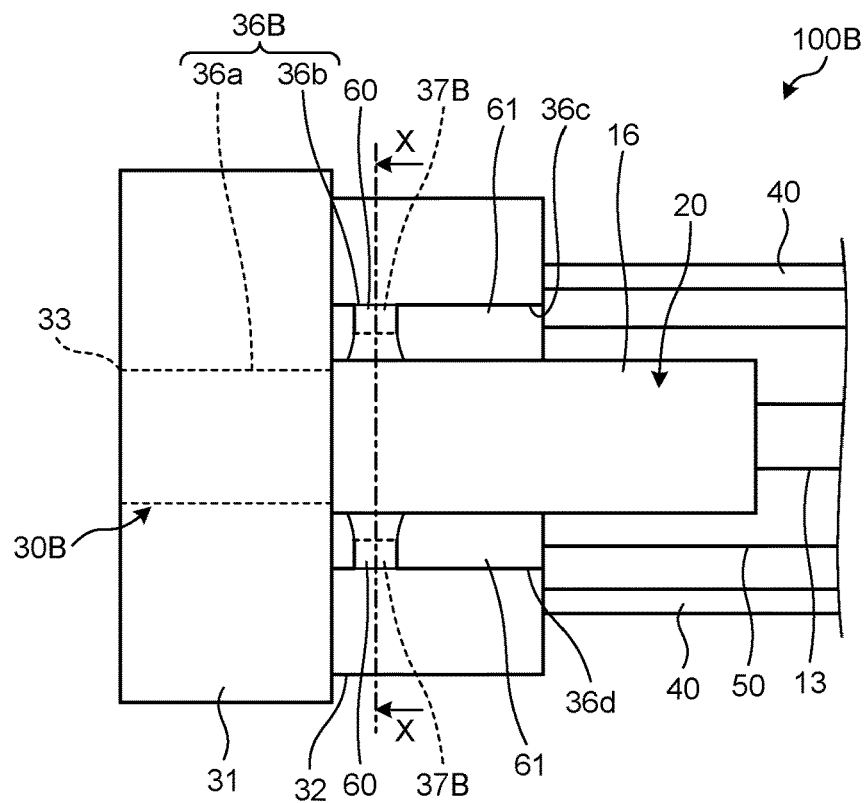
FIG. 6A is a top view of an endoscope front-end structure according to a second modification example of the embodiment of the disclosure and FIG. 6B is an X-X cross sectional view of an endoscope front-end structure according to a second modification example of the embodiment of the disclosure.
Figure 6B:
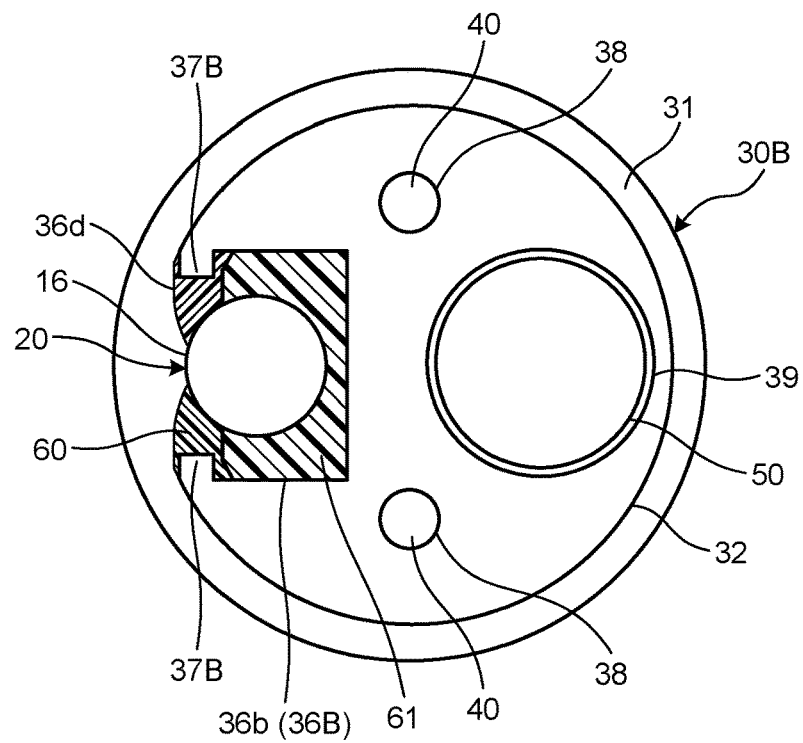

Meanwhile, the positions for forming the salient portions 37 or the salient portions 37A are not limited to the central part of the opening 36d, and alternatively can be formed on the side of the front-end frame portion 31. FIG. 6A is a top view of an endoscope front-end structure 100B according to a second modification example of the embodiment of the disclosure; and FIG. 6B is a cross sectional view taken along X-X line illustrated in FIG. 6A.

In the endoscope front-end structure 100B according to the second modification example, in the through hole 36b (36B) of a frame body 30B, salient portions 37B are formed on the side of the front-end frame portion 31. That is, the salient portions 37B are formed at positions closer to the front-end frame portion 31 as compared to the salient portions 37 explained with reference to FIG. 4A. The salient portions 37B have an identical shape to the shape of the salient portions 37. As a result of forming the salient portions 37B, it becomes possible to achieve the same effects as achieved according to the embodiment. Moreover, since it suffices to supply the second adhesive agent 61 into the through hole 36B only from the side of the proximal end, the filling task becomes easier. Meanwhile, in the endoscope front-end structure 100B too, the cross sectional view perpendicular to the optical axis direction of the proximal-end frame portion 32, in which the salient portions 37B are not formed, has an identical structure to the structure illustrated in FIG. 4C.

In the second embodiment, although the salient portions 37B are formed at positions closer to the front-end frame portion 31, they can alternatively be formed closer to the proximal end of the proximal-end frame portion 32.

Figure 7A:
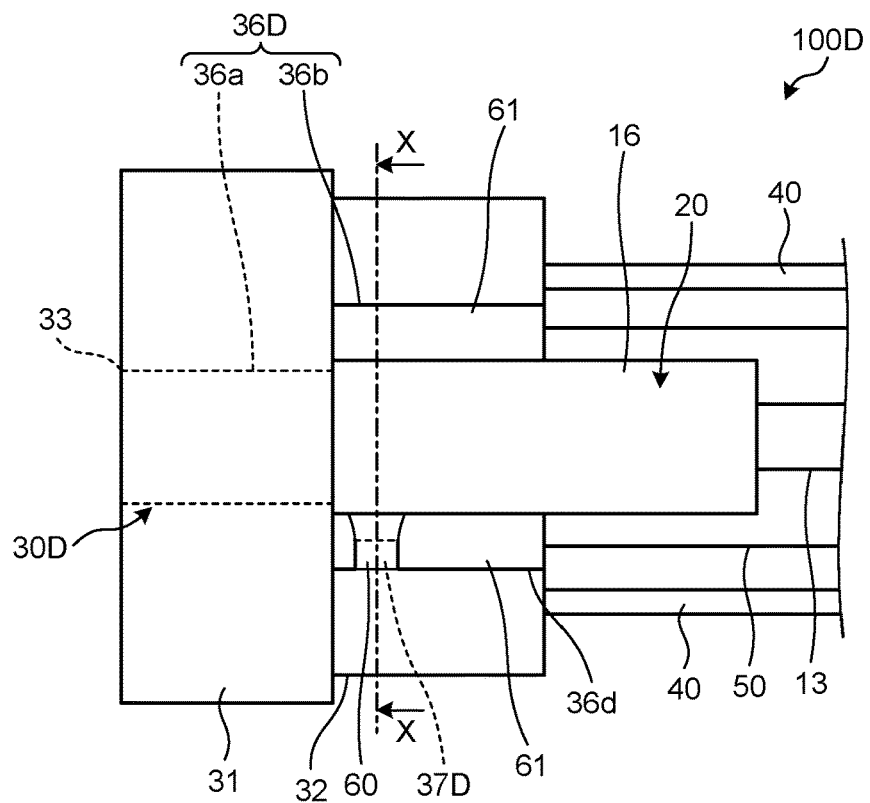
FIG. 7A is a top view of an endoscope front-end structure according to a third modification example of the embodiment of the disclosure and FIG. 7B is an X-X cross sectional view of an endoscope front-end structure according to a third modification example of the embodiment of the disclosure.
Figure 7B:
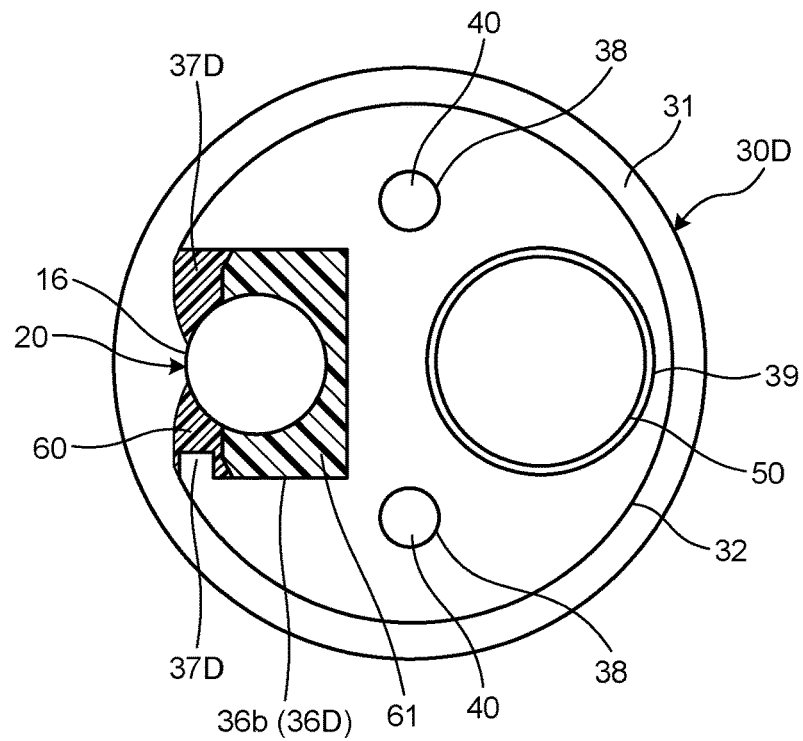

Moreover, it is not always necessary to form two salient portions 37 facing each other. Alternatively, only a single salient portion 37 can be formed. FIG. 7A is a top view of an endoscope front-end structure 100D according to a third modification example of the embodiment of the disclosure; and FIG. 7B is a cross sectional view taken along X-X line illustrated in FIG. 7A.

In the endoscope front-end structure 100D according to the third modification example, in the through hole 36b (36D) of a frame body 30D, only a single salient portion 37D is formed at a position on a side that is parallel to the optical axis of the opening 36d and that is on the side of the front-end frame portion 31. That is, the salient portion 37D is formed at a position closer to the front-end frame portion 31. The salient portion 37D has an identical shape to the shape of the salient portions 37. As a result of forming only a single salient portion 37D on one side, there is a slight deterioration from the perspective of positional accuracy as compared to the case in which the salient portions 37 are formed opposite to each other as explained in the embodiment. On the other hand, since it suffices to supply the second adhesive agent 61 into the through hole 36b only from the side of the proximal end, the filling task becomes easier. Meanwhile, in the endoscope front-end structure 100D too, the cross sectional view perpendicular to the optical axis direction of the proximal-end frame portion 32, in which the salient portion 37D is not formed, has an identical structure to the structure illustrated in FIG. 4C.

Figure 8A:
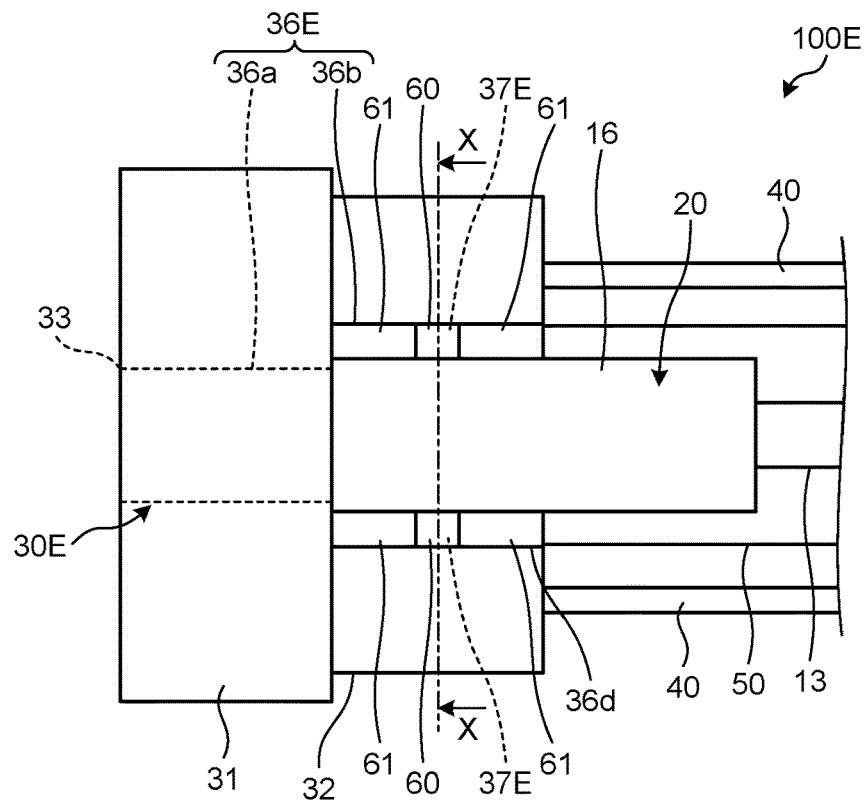
FIG. 8A is a top view of an endoscope front-end structure according to a fourth modification example of the embodiment of the disclosure and FIG. 8B is an X-X cross sectional view of an endoscope front-end structure according to a fourth modification example of the embodiment of the disclosure.
Figure 8B:
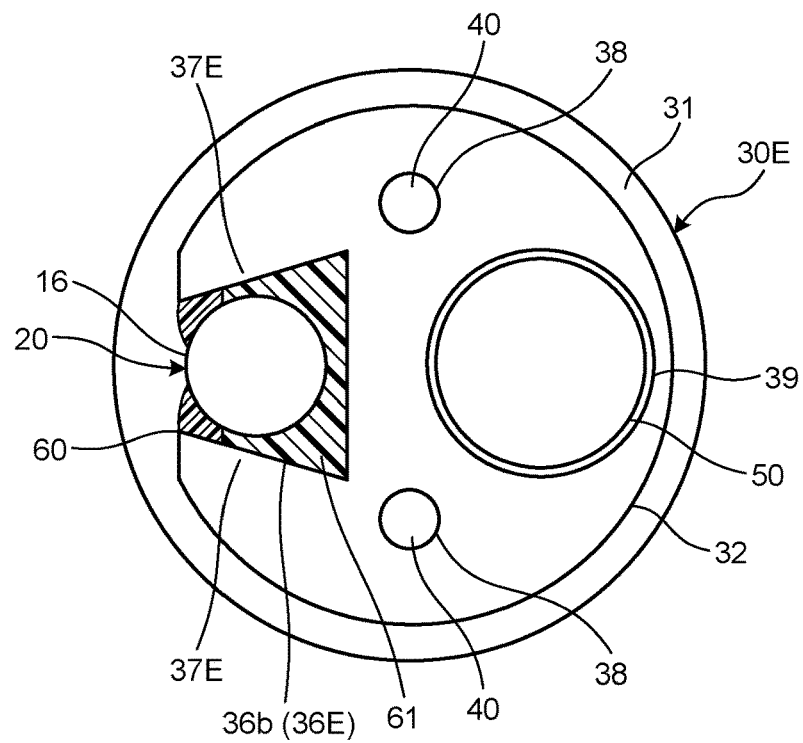

Moreover, as long as a salient portion protrudes from the inner surface of the through hole for enabling partial shortening of the distance between the salient portion and the resin seal 16 of the imaging module 20 as well as for enabling an increase in the connection area with the first adhesive agent 60, it serves the purpose. FIG. 8A is a top view of an endoscope front-end structure 100E according to a fourth modification example of the embodiment of the disclosure; and FIG. 8B is a cross sectional view taken along X-X line illustrated in FIG. 8A.

In the endoscope front-end structure 100E according to the fourth modification example, in the through hole 36b (36E) of a frame body 30E, salient portions 37E are formed to narrow an opening width of the through hole 36E toward the opening 36d from the bottom of the through hole 36E. That is, the salient portions 37E are formed to have a tapering shape. As a result of forming the salient portions 37E, the first adhesive agent 60 can be applied only in between the central part of each salient portion 37E and the resin seal 16. With that, the amount of usage of the first adhesive agent 60 can be reduced; the first adhesive agent 60 can be prevented from leaching out in the area meant for filling the second adhesive agent 61; and the risk of breakage of the imager 11 can be reduced when there is stress acting on the endoscope front-end structure 100E. Meanwhile, in the endoscope front-end structure 100E too, the cross sectional view perpendicular to the optical axis direction of the proximal-end frame portion 32, in which the salient portions 37E are not formed, has an identical structure to the structure illustrated in FIG. 4C.

In the embodiment and the modification examples described above, the opening 36d is formed across the entire lateral face of the proximal-end frame portion 32. Alternatively, an opening can be formed while retaining some portion of the lateral face on the side of the proximal end.

According to the disclosure, it becomes possible to prevent a position misalignment of the imaging module inside the frame body, and thus the imaging module can be assembled inside the frame body with a precise positional accuracy.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope front-end structure comprising:
   an imaging module comprising:
      an optical assembly configured to form an image of a photographic subject,
      an image sensor configured to generate an image signal of a photographic subject image, which is formed by the optical assembly, and
      a cable configured to transmit the image signal; and
   a frame body comprising:
      an opening formed in a circumferential surface of the frame to extend along an optical axis direction,
      a through hole passing through the frame body in the optical axis direction to define an internal space housing the imaging module, and
      a salient portion,
   wherein the internal space communicating with an outside of the frame body through the opening,
   the salient portion protruding from an inner surface of the frame body toward the imaging module housed in the internal space, the inner surface forming the internal space, the salient portion being formed to project from a side of the opening, the side being parallel to the optical axis direction,
   a first adhesive agent and a second adhesive agent different from the first adhesive agent being filled and hardened in the internal space in which the imaging module is housed such that the imaging module is embedded and fixed in the first adhesive agent hardened and the second adhesive agent hardened,
   the first adhesive agent being filled and hardened between a resin seal and the salient portion at a position corresponding to the salient portion to cover a surface of the salient portion, the resin seal being configured to seal a portion spanning from a proximal end of a lateral face of the optical assembly to a junction of the cable; and
   the second adhesive agent being filled and hardened in the internal space other than an area filled with the first adhesive agent.

2. The endoscope front-end structure according to claim 1, wherein the salient portion includes two salient portions that face each other.

3. The endoscope front-end structure according to claim 1, wherein the second adhesive agent has a lower degree of post-hardening hardness than a degree of post-hardening hardness of the first adhesive agent.

4. The endoscope front-end structure according to claim 1, wherein the first adhesive agent has a higher degree of pre-hardening viscosity than a degree of pre-hardening viscosity of the second adhesive agent.

5. The endoscope front-end structure according to claim 1, wherein the first adhesive agent is an ultraviolet cure adhesive, and the second adhesive agent is a thermoset adhesive agent.

6. An endoscope comprising the endoscope front-end structure according to claim 1.

7. The endoscope front-end structure according to claim 1, wherein a height of the salient portion is 50% to 70% of a distance between the side of the opening and an outer surface of the imaging module.

8. The endoscope front-end structure according to claim 1, wherein the salient portion being formed at a central part of the side of the opening.

* * * * *